United States Patent
Brannan et al.

(10) Patent No.: US 9,375,273 B2
(45) Date of Patent: Jun. 28, 2016

(54) SYSTEM AND METHOD FOR CHECKING HIGH POWER MICROWAVE ABLATION SYSTEM STATUS ON STARTUP

(75) Inventors: Joseph D. Brannan, Erie, CO (US);
Jeffrey L. Jensen, Boulder, CO (US);
Darion Peterson, Boulder, CO (US);
Kyle R. Rick, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1904 days.

(21) Appl. No.: 12/562,575

(22) Filed: Sep. 18, 2009

(65) Prior Publication Data
US 2011/0071511 A1    Mar. 24, 2011

(51) Int. Cl.
*A61B 18/18*    (2006.01)
*A61B 18/12*    (2006.01)
*A61B 17/00*    (2006.01)
*A61B 18/00*    (2006.01)
*A61N 5/02*    (2006.01)

(52) U.S. Cl.
CPC ......... *A61B 18/1815* (2013.01); *A61B 18/1206* (2013.01); *A61B 2017/00119* (2013.01); *A61B 2017/00154* (2013.01); *A61B 2017/00725* (2013.01); *A61B 2018/00577* (2013.01); *A61B 2018/00702* (2013.01); *A61B 2018/00898* (2013.01); *A61N 5/02* (2013.01)

(58) Field of Classification Search
CPC .......... A61B 2018/00702; A61B 2018/00898; A61B 2018/00648
USPC .................................... 606/34, 38
See application file for complete search history.

(56) References Cited

U.S. PATENT DOCUMENTS

| | | | | |
|---|---|---|---|---|
| 5,304,214 A | * | 4/1994 | DeFord et al. | 607/105 |
| 5,575,789 A | * | 11/1996 | Bell et al. | 606/42 |
| 6,002,968 A | * | 12/1999 | Edwards | 607/101 |
| 6,312,391 B1 | | 11/2001 | Ramadhyani et al. | |
| 6,955,672 B2 | * | 10/2005 | Cense et al. | 606/9 |
| 7,481,809 B2 | * | 1/2009 | Stern et al. | 606/41 |
| 8,242,782 B2 | * | 8/2012 | Brannan et al. | 324/415 |
| 2004/0010289 A1 | * | 1/2004 | Biggs et al. | 607/2 |
| 2005/0010206 A1 | | 1/2005 | Nasab et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 12/129,482, filed May 29, 2008.

(Continued)

*Primary Examiner* — Jocelyn D Ram (57) ABSTRACT

A microwave ablation system includes a generator operable to output energy and an ablation probe coupled to the generator that delivers the energy to a tissue region. The ablation system also includes a controller operable to control the generator and at least one sensor coupled to the ablation probe and the controller that detects an operating parameter of the ablation probe. The controller performs a system check by ramping up an energy output of the generator from a low energy level to a high energy level and monitors an output from the sensor at predetermined intervals of time during the system check to determine an abnormal state. The controller controls the generator to cease the energy output when the controller determines an abnormal state.

6 Claims, 7 Drawing Sheets

(56) References Cited

U.S. PATENT DOCUMENTS

| | | | |
|---|---|---|---|
| 2007/0050000 A1* | 3/2007 | Esch et al. ............... | 607/96 |
| 2007/0173805 A1* | 7/2007 | Weinberg et al. .......... | 606/34 |
| 2008/0039746 A1 | 2/2008 | Hissong et al. | |
| 2008/0077126 A1* | 3/2008 | Rashidi ..................... | 606/34 |
| 2009/0234353 A1* | 9/2009 | McPherson ................. | 606/35 |
| 2012/0130256 A1* | 5/2012 | Buysse et al. .............. | 600/476 |
| 2012/0150170 A1* | 6/2012 | Buysse et al. .............. | 606/34 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-1106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO0174252 | 10/2001 |
| WO | WO02085229 | 10/2002 |
| WO | WO2004083797 | 9/2004 |
| WO | WO2008002517 | 1/2008 |
| WO | WO2009075879 | 6/2009 |

OTHER PUBLICATIONS

U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.

(56) References Cited

OTHER PUBLICATIONS

U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list). 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000. Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2. No. 5, pp. 399-404.
H. Schwarzmaier et al.. "Magnetic Resonance Imaging of Microwave Induced Tissue Heating" Dept. of Laser Medicine & Dept. of Diagnostic Radiology; Heinrich-Heine-University, Duesseldorf. Germany; Dec. 8. 1994; pp. 729-731.
Heniford et al.. "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finitellement Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic. and Laparoscopic Surgery, Sales/Product Literature, Jan. 2004.
Livraghi et al., (1995) "Saline-enhanced RF Tissue Ablation in the Treatment of Liver Metastases", Radiology, pp. 205-210.

(56) References Cited

OTHER PUBLICATIONS

Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Dec. 1999) "FlexStrand": product description, 1 page.
Mdtech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(2005.03); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology. vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl I):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.

(56) References Cited

OTHER PUBLICATIONS

European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Reprot EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
european Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. Ii, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP10009732 dated Jan. 26, 2011.

* cited by examiner

SYSTEM AND METHOD FOR CHECKING HIGH POWER MICROWAVE ABLATION SYSTEM STATUS ON STARTUP

BACKGROUND

1. Technical Field

The present disclosure relates generally to microwave ablation procedures that utilize microwave surgical devices having a microwave antenna which may be inserted directly into tissue for diagnosis and treatment of diseases. More particularly, the present disclosure is directed a system and method for verifying correct system operation prior to high power energy delivery by the microwave antenna.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 mHz to about 10 gHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

Microwave ablation devices utilize sensors to determine if the system is working properly. However, without delivery of microwave energy, the sensors may indicate that the probe assembly status is normal. Further, defects in antenna assemblies may not be apparent except at high powers. As such, when microwave ablation system is tested using a low power routine a post manufacture defect may not be apparent. This is especially important for high power microwave ablation devices, where failures may result in extremely high temperatures.

SUMMARY

The present disclosure provides a microwave ablation system. The microwave ablation system includes a generator operable to output energy, an ablation probe coupled to the generator that is operable to deliver the energy to a tissue region, a controller operable to control the generator, and at least one sensor coupled to the ablation probe and the controller. The sensor detects an operating parameter of the ablation probe. The controller performs a system check by ramping up an energy output of the generator from a low energy level to a high energy level and monitors an output from the at least one sensor at predetermined intervals of time during the system check to determine an abnormal state. The controller controls the generator to cease the energy output when the controller determines an abnormal state.

In another embodiment of the microwave ablation system, the at least one sensor detects a temperature of the ablation probe.

In yet another embodiment of the microwave ablation system, the at least one sensor is a thermocouple, thermistor, or optical fiber.

In yet another embodiment of the microwave ablation system, the at least one sensor detects a radiating behavior.

In yet another embodiment of the microwave ablation system, the at least one sensor is a receiving antenna or rectenna.

In yet another embodiment of the microwave ablation system, the at least one sensor detects forward and/or reflected power.

In yet another embodiment of the microwave ablation system, the at least one sensor is a radio frequency power sensor.

In yet another embodiment of the microwave ablation system, the at least one sensor detects fluid pressure.

In yet another embodiment of the microwave ablation system, the at least one sensor is a pressure sensor.

In yet another embodiment of the microwave ablation system, the at least one sensor detects air bubbles.

In yet another embodiment of the microwave ablation system, the at least one sensor is an optical sensor.

The present disclosure also provides a method of detecting an abnormal state in a microwave ablation system. The method includes the steps of outputting a low energy level from a generator to an ablation probe and detecting an operational parameter of the ablation probe at the low energy level. The detected operational parameter is compared to a predetermined range for the operational parameter and an energy level output of the generator is increased in response to the comparison. The microwave ablation system ceases output of energy from the generator in response to the detected operational parameter being outside the predetermined range.

In yet another embodiment, the operational parameter is a temperature of the ablation probe.

In yet another embodiment, the operational parameter is a radiating behavior.

In yet another embodiment, the operational parameter is forward power or reflected power.

In yet another embodiment, the operational parameter is fluid pressure.

In yet another embodiment, the operational parameter is the presence of air bubbles.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. The phrase "ablation procedure" generally refers to any ablation procedure, such as RF or microwave ablation or microwave ablation assisted resection. The phrase "transmission line" generally refers to any transmission medium that can be used for the propagation of signals from one point to another.

Figure 1:
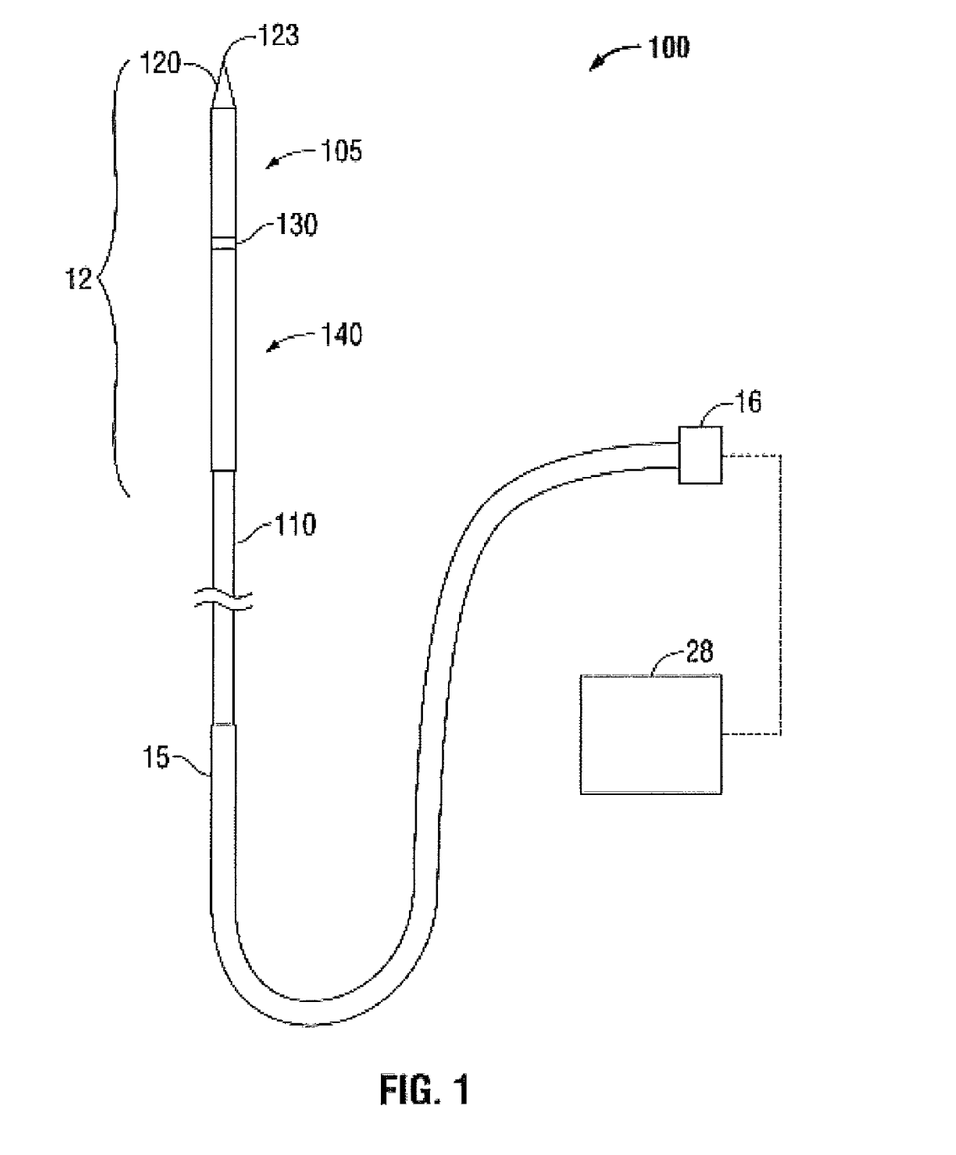
FIG. 1 shows a representative diagram of a variation of a microwave antenna assembly in accordance with an embodiment of the present disclosure.

FIG. 1 shows a microwave antenna assembly 100 in accordance with one embodiment of the present disclosure. Antenna assembly 100 includes a radiating portion 12 that is connected by feedline 110 (or shaft) via cable 15 to connector 16, which may further connect the assembly 100 to a power generating source 28, e.g., a microwave or RF electrosurgical generator. Assembly 100, as shown, is a dipole microwave antenna assembly, but other antenna assemblies, e.g., monopole or leaky wave antenna assemblies, may also utilize the principles set forth herein. Distal radiating portion 105 of radiating portion 12 includes a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, cylindroconical or any other polygonal shape.

Figure 4A:
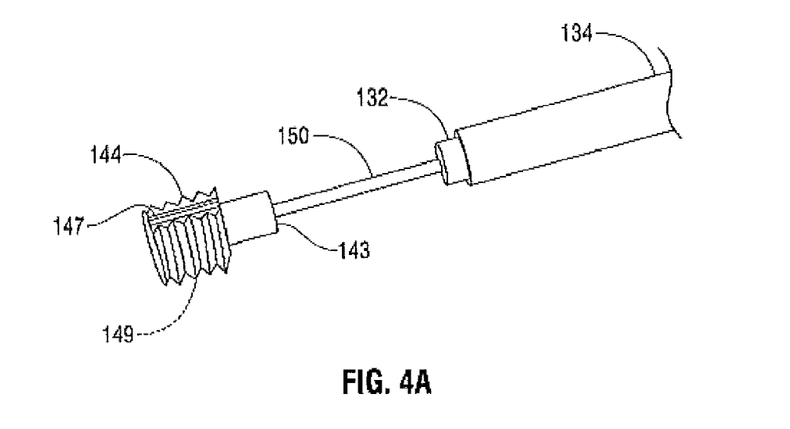
FIGS. 4A-4D show perspective views of an embodiment of a distal portion of a microwave antenna in various stages of assembly.
Figure 4B:
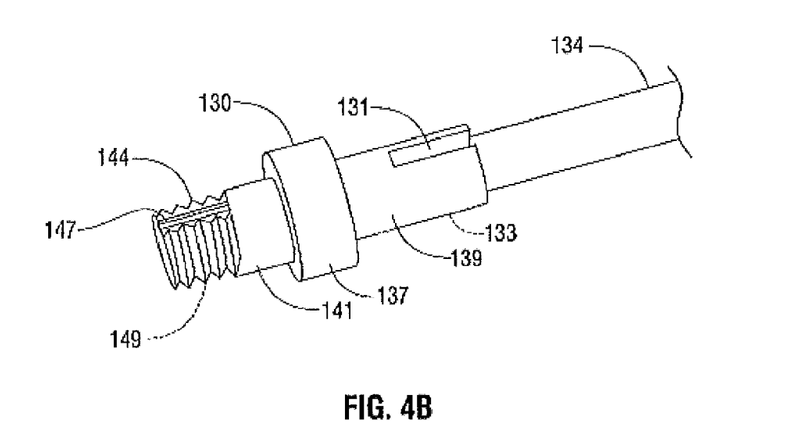

An insulating puck 130 is disposed between distal radiating portion 105 and proximal radiating portion 140. Puck 130 may be formed from any suitable elastomeric or ceramic dielectric material by any suitable process. In embodiments, the puck 130 is formed by overmolding from polyether block amide (e.g., Pebax® sold by Arkema), polyetherimide (e.g., Ultem® and/or Extern° sold by SABIC Innovative Plastics), polyimide-based polymer (e.g., Vespel® sold by DuPont), or ceramic. As best illustrated in FIG. 4B, puck 130 includes coolant inflow port 131 and coolant outflow port 133 to respectively facilitate the flow of coolant into, and out of, coolant chamber 148 of trocar 122 as further described hereinbelow.

With reference now to FIGS. 2, 3, and 4A-4D, distal radiating portion 105 includes a trocar 122 having a generally cylindroconical shape. Proximal radiating portion 140 includes a proximal antenna member 128 having a generally cylindrical shape. Additionally or alternatively, proximal antenna member 128 may have a generally square or hexagonal shape. Trocar 122 and proximal antenna member 128 may be formed from a variety of biocompatible heat resistant conductive materials suitable for penetrating tissue, such as without limitation, stainless steel. Antenna assembly 110 includes a coaxial transmission line 138 having, in coaxial disposition, an inner coaxial conductor 150, an intermediate coaxial dielectric 132, and an outer coaxial conductor 134. Nominally, coaxial transmission line 138 has an impedance of about 50 ohms. Inner coaxial conductor 150 and outer coaxial conductor 134 may be formed from any suitable electrically conductive material. In some embodiments, inner coaxial conductor 150 is formed from stainless steel and outer coaxial conductor 132 is formed from copper. Coaxial dielectric 132 may be formed from any suitable dielectric material, including without limitation, polyethylene terephthalate, polyimide, or polytetrafluoroethylene (PTFE) (e.g., Teflon®, manufactured by E. I. du Pont de Nemours and Company of Wilmington, Del., United States). Inner coaxial conductor 150 may be electrically coupled to trocar 122 and outer coaxial conductor 134 may be electrically coupled to proximal antenna member 128.

Figure 2:
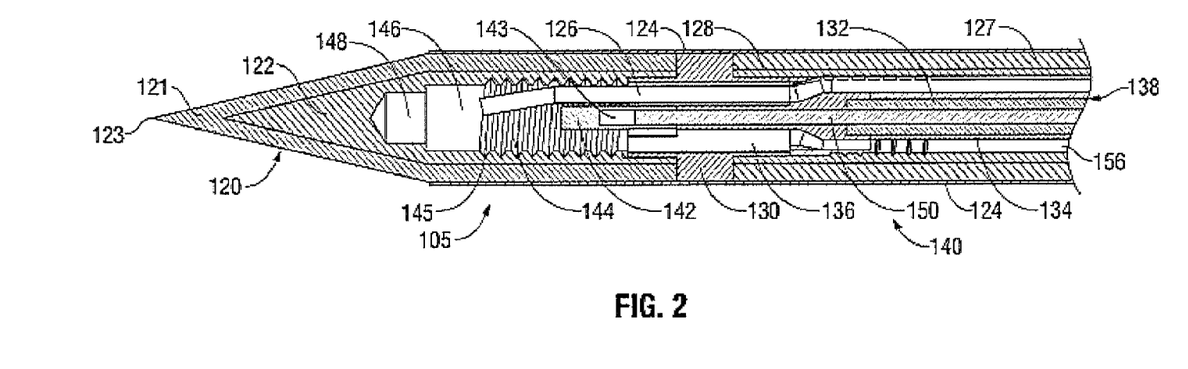
FIG. 2 shows a cross-sectional view of a representative variation of a distal end of microwave antenna assembly in accordance with another embodiment of the present disclosure.
Figure 3:
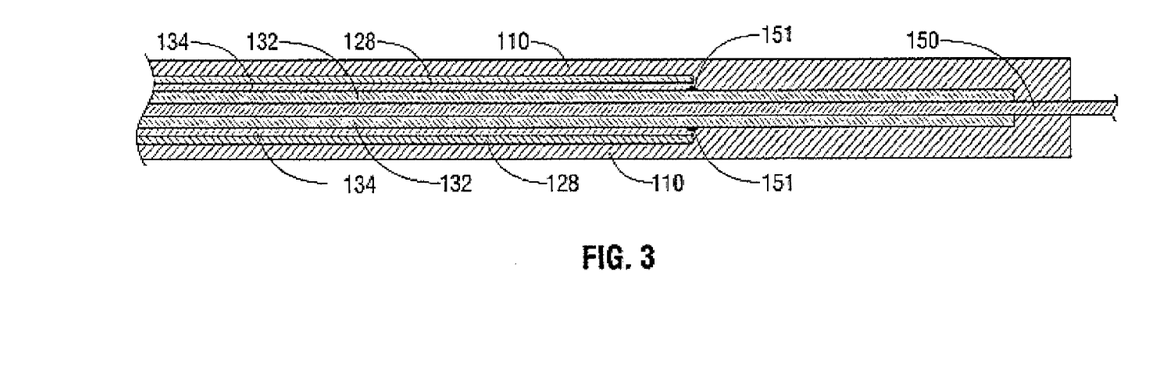
FIG. 3 shows a cross-sectional view of a representative variation of a proximal end of microwave antenna assembly in accordance with another embodiment of the present disclosure.

A longitudinal opening 146 is defined within trocar 122 and opens to a proximal end thereof, and defines a cooling chamber 148 and a threaded section 145 within trocar 122. Cooling chamber 148 may have a generally cylindrical shape and, additionally or alternatively, may have a stepped, tapered, conical, or other shape that is generally dimensioned in accordance with the shape of the tapered end 120 of the cylindroconical profile of trocar 122 to permit the flow of coolant to more effectively reach the distal regions of trocar 122. Additionally or alternatively, cooling chamber may have a square, hexagonal, or any suitable shape. The dielectric properties of sterile water or saline flowing through cooling chamber 148 may enhance the overall ablation pattern of antenna assembly 100.

A coolant inflow tube 126 is in operable fluid communication at a proximal end thereof with a source of cooling fluid (not explicitly shown), and, at a distal end thereof, coolant inflow tube 126 is in fluid communication with cooling chamber 148 to provide coolant thereto. Coolant inflow tube 126 may be formed from any suitable material, e.g., a polymeric material, such as without limitation, polyimide. In an embodiment, coolant inflow tube 126 passes through coolant inflow port 131. In some embodiments, a coolant outflow channel 136 may be provided to facilitate removal of coolant from cooling chamber 146, through antenna assembly 100, to a collection reservoir (not explicitly shown). The coolant may be any suitable fluid, such as without limitation water, sterile water, deionized water, and/or saline.

Threaded section 145 of trocar 122 is configured to receive trocar screw 144. Trocar screw 144 includes at the proximal end thereof an opening 143 defined therein that is configured to accept the distal end of inner coaxial conductor 150. In embodiments, distal end of inner coaxial conductor 150 is fixed within opening 143 by any suitable manner of electromechanical attachment, such as without limitation welding, brazing, and/or crimping. As seen in FIG. 4A, an inflow groove 147 and an outflow groove 149 are disposed longitudinally through the threaded portion of trocar screw 144 to respectively facilitate the flow of coolant into, and out of, cooling chamber 148. Inflow groove 147 and outflow groove 149 may be configured to accommodate the insertion of coolant inflow tube 126 and/or a corresponding outflow tube (not explicitly shown). A return path 156 in the antenna assembly may additionally or alternatively provide an exit conduit for the cooling fluid.

In the illustrated embodiment, trocar 122 and proximal antenna member 128 include a dielectric coating 121, 127, respectively, on the respective outer surfaces thereof. The dielectric coating 121, 127 may include any suitable dielectric material, such as without limitation, ceramic material. In some embodiments, dielectric coating 121, 127 may be formed from titanium dioxide and/or zirconium dioxide. Dielectric coating 121, 127 may be applied to trocar 122 and/or proximal antenna member 128 by any suitable process, for example without limitation, plasma spraying or flame spraying. In embodiments, dielectric coating 121, 127 has a thickness in the range of about 0.005 inches to about 0.015 inches. During an ablation procedure, the dielectric coating 121, 127 may provide improved dielectric matching and/or improved dielectric buffering between the antenna and tissue, which may enable the use of higher power levels, which, in turn, may enable a surgeon to achieve greater ablation rates resulting in increased ablation size, reduced operative times, and/or improved operative outcomes.

An outer jacket 124 is disposed about the outer cylindrical surface of antenna assembly 100, e.g., the distal radiating portion 105, puck 130, and proximal radiating section 140. Outer jacket 124 may be formed from any suitable material, including without limitation polymeric or ceramic materials. In some embodiments, outer jacket 124 is formed from PTFE. Outer jacket 124 may be applied to antenna assembly 100 by any suitable manner, including without limitation, heat shrinking.

Continuing with reference to FIGS. 4A-4D, a method of manufacturing antenna assembly 100 is disclosed wherein inner coaxial conductor 150 is inserted into opening 143 of trocar screw 144. Inner coaxial conductor 150 is electrically fixed to trocar screw 144 by any suitable manner of bonding, such as without limitation, laser welding, brazing, or crimping. The coaxial transmission line 138 and trocar screw 144 subassembly is placed in a mold (not explicitly shown), such as without limitation an injection micro-mold, that is configured to overmold the puck 130. Advantageously, inflow groove 147 and outflow groove 149 are aligned with mold features (not explicitly shown) corresponding to coolant inflow port 131 and coolant outflow port 133 such that, when molded, a continuous fluid connection is formed between inflow groove 147 and coolant inflow port 131, and between outflow groove 149 and outflow port 133.

Puck material, e.g., ceramic, Pebax®, Ultem®, Extem®, Vespel®, or any suitable polymer having dielectric properties, is shot into the mold, allowed to cool/and or set, and subsequently released from the mold to form an assembly that includes puck 130, trocar screw 143 and coaxial transmission line 138 as best illustrated in FIG. 4B. The formed puck 130 includes a center section 137 having an outer diameter corresponding to the outer diameters of trocar 122 (inclusive of the thickness of dielectric coating 121) and/or proximal antenna member 128 (inclusive of the thickness of dielectric coating 127). Puck 130 further includes a distal shoulder 141 having an outer diameter corresponding to the inner diameter of trocar 122, and a proximal shoulder 139 having an outer diameter corresponding to the inner diameter of proximal antenna member 128.

Figure 4C:
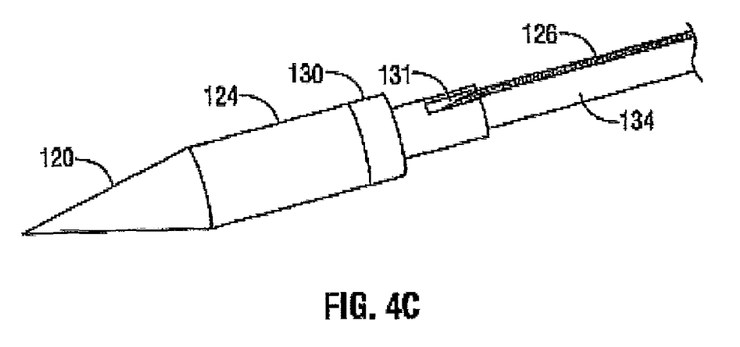
Figure 4D:
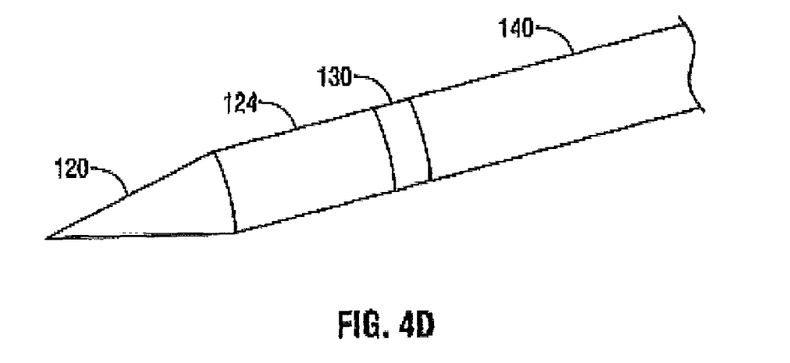

Trocar 122 may then be threaded onto trocar screw 144 to form the distal radiating section 120, as best shown in FIG. 4C. Inflow tube 126 may then be inserted into coolant inflow port 131. Proximal antenna member 128 may then be positioned against puck 130 such that the distal end of proximal antenna member 128 engages the proximal shoulder of puck 130, thus forming a sealed proximal radiation section 140.

Tension may be applied to inner coaxial conductor 150 and/or dielectric 132 in a proximal direction, thereby drawing together distal radiating section 105, puck 130, and proximal radiating section 140, and placing puck 130 in a state of compression. Inner coaxial conductor 150 and/or dielectric 132 may be fixed in a state of tension at an anchor point 151, by any suitable manner of fixation, including without limitation spot welding, brazing, adhesive, and/or crimping. In this manner, the antenna sections are "locked" together by the tensile force of inner coaxial conductor 150 and/or dielectric 132, which may result in improved strength and stiffness of the antenna assembly.

Outer jacket 124 may be applied to the outer surface of radiating portion 12 by any suitable method, for example without limitation, heat shrinking, overmolding, coating, spraying, dipping, powder coating, baking and/or film deposition.

It is contemplated that the steps of a method in accordance with the present disclosure can be performed in a different ordering than the ordering provided herein.

Figure 5A:
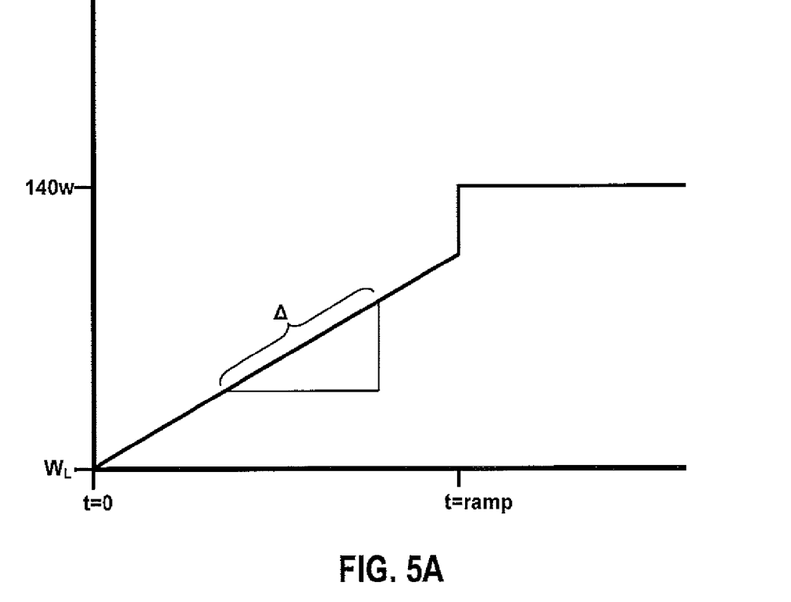
FIGS. 5A-5C show graphs of time versus power in accordance with embodiments of the present disclosure.

FIG. 5A is a graph depicting an operation of the microwave ablation system according to an embodiment of the invention. As depicted in FIG. 5, at t=0, the energy output from the generator is $W_L$ that may be a low wattage or 0 W. As t increases, the energy output also increases at a constant slope $\Delta$. Slope $\Delta$ is sufficient to prevent any harm to a clinician or patient and to prevent and damage to the system. When t=ramp, with ramp being a value of time sufficient to determine if the microwave ablation system is malfunctioning, the energy output increases to an energy level, e.g., 140 W, sufficient to perform a microwave ablation procedure. During the ramping procedure (0<t<ramp), the microwave ablation system performs a system check to determine if the system is in proper working order or if it is malfunctioning. If the system is malfunctioning, an energy output from the generator is ceased thereby preventing any harm to a clinician or patient or preventing any further damage to the microwave ablation system.

Figure 5B:
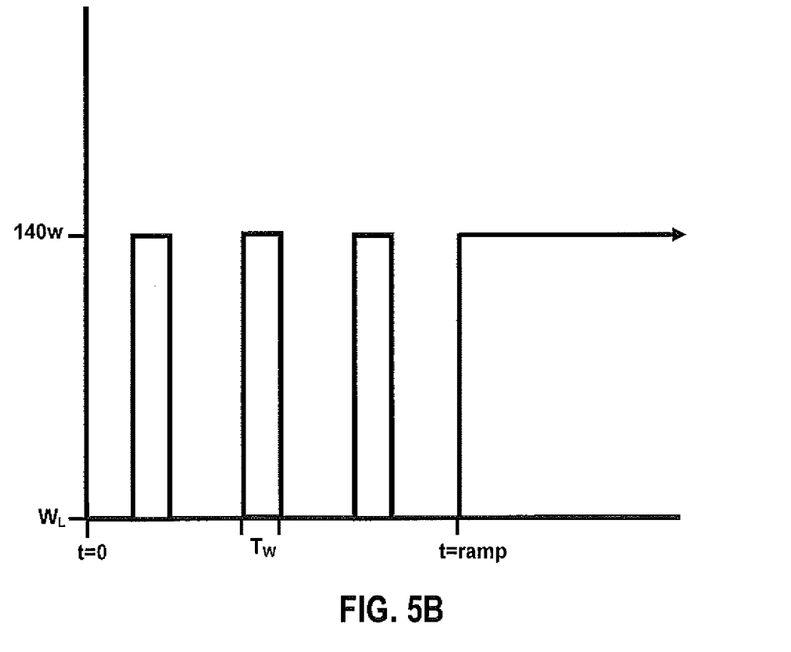
Figure 5C:
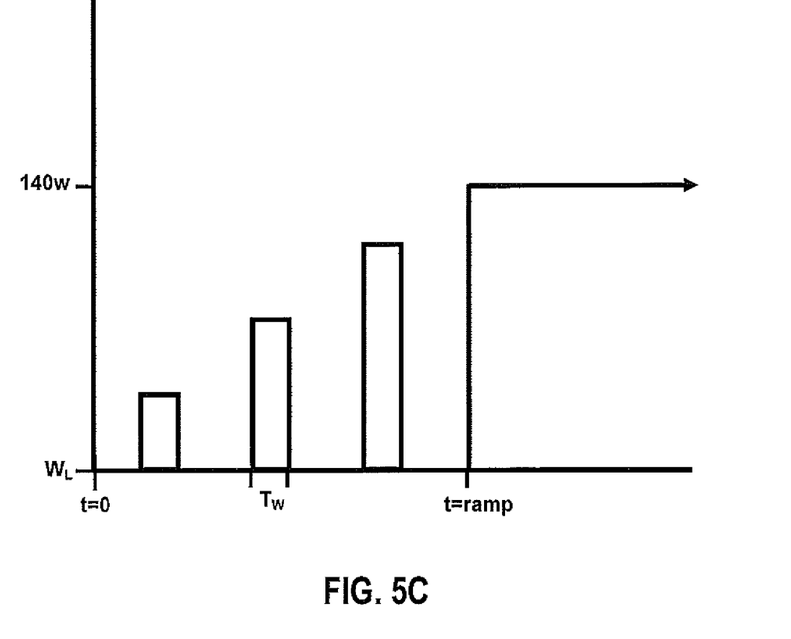

Alternatively, as shown in FIGS. 5B and 5C, a series of pulses may be used during the start up procedure. As shown in FIG. 5B, the series of pulses have a constant amplitude with a pulse width $T_W$. A duty cycle for the pulses may be varied in order to adequately check the system without harming the patient or the clinician. Alternatively, as shown in FIG. 5C, the series of pulses during the start up procedure may have a pulse width $T_W$ and vary in amplitude. The amplitude of the pulses may gradually reach an energy level sufficient to perform a microwave ablation procedure.

By utilizing a system check which gradually subjects the device to increasing operational stresses while monitoring sensor status will allow for microwave ablation systems to limit the number of devices which are damaged due to operator error, such as not turning on the cooling fluid pump. It will also reduce the likelihood of patient and/or user injury from potentially defective assemblies or from user error.

Figure 6:
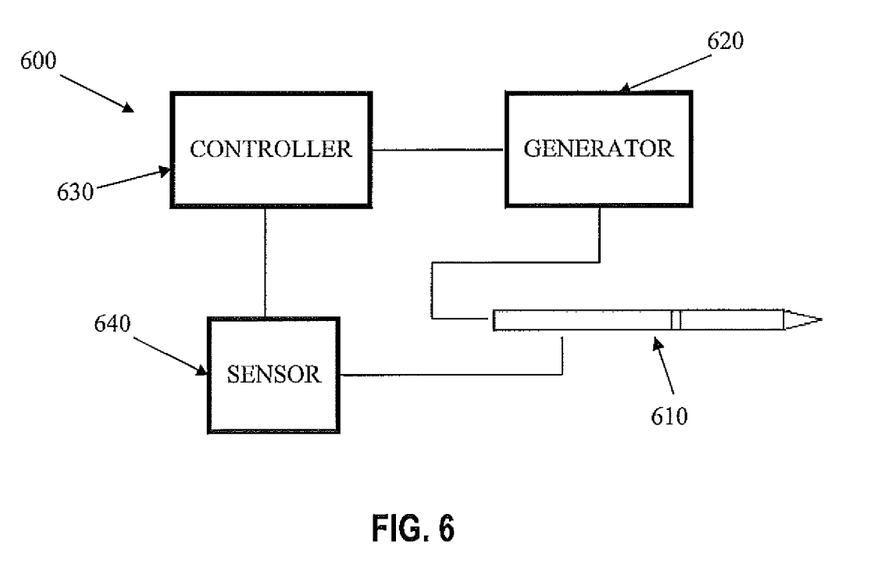
FIG. 6 shows a system block diagram according to an embodiment of the present disclosure.

With reference to FIG. 6, a microwave ablation system, shown generally as 600, according to an embodiment of the disclosure is depicted. System 600 has an antenna assembly 610 that imparts microwave energy to a patient. Antenna assembly 610 is substantially similar to antenna assembly 100 described above. Generator 620, which is substantially similar to power generating source 28, is coupled to antenna assembly 610 and provides a source of energy thereto. Controller 630 is coupled to generator 620 and is configured to control generator 620 based on an input or signal from sensor 640. Controller 630 may be a microprocessor or any logic circuit able to receive an input or signal from sensor 640 and provide an output to control generator 620. Sensor 640 may be a single sensor or an array of sensors to detect operational parameters of the antenna assembly 610 in order to determine if the microwave ablation system 600 is functioning properly. If the sensor 640 detects an abnormal value or level, the controller 630 controls the generator 620 to cease an energy output. Sensor 640 may be incorporated into antenna assembly 610 or controller 630 or may be coupled to either antenna assembly 610 and/or controller 630. Microwave ablation system 600 may also be incorporated in antenna assembly 610 or may be arranged in two or more devices. For instance, controller 630 and generator 620 may be incorporated in a single device or may be separate devices.

Sensor 640 may be a temperature sensor to detect the temperature of the antenna assembly 610. Temperature sensor may be a thermocouple, thermistor or an optical fiber. A thermocouple is a junction between two different metals that produces a voltage related to a temperature difference. Thermocouples are can also be used to convert heat into electric power. Any circuit made of dissimilar metals will produce a temperature-related difference of voltage. Thermocouples for practical measurement of temperature are made of specific alloys, which in combination have a predictable and repeatable relationship between temperature and voltage. Different alloys are used for different temperature ranges and to resist corrosion. Where the measurement point is far from the measuring instrument, the intermediate connection can be made by extension wires, which are less costly than the materials used to make the sensor. Thermocouples are standardized against a reference temperature of 0 degrees Celsius. Electronic instruments can also compensate for the varying characteristics of the thermocouple to improve the precision and accuracy of measurements.

A thermistor is a type of resistor whose resistance varies with temperature. Thermistors are widely used as inrush current limiters, temperature sensors, self-resetting overcurrent protectors, and self-regulating heating elements. The material used in a thermistor is generally a ceramic or polymer. Thermistors typically achieve a high precision temperature response within a limited temperature range.

Sensor 640 may also be used to monitor radiating behavior. Such sensor may be a receiving antenna or a rectenna. The receiving antenna receives radiation from the antenna assembly and provides an electrical signal to indicate the level of radiation. A rectenna is a rectifying antenna, a special type of antenna that is used to directly convert microwave energy into DC electricity. Its elements are usually arranged in a multi element phased array with a mesh pattern reflector element to make it directional. A simple rectenna can be constructed from a Schottky diode placed between antenna dipoles. The diode rectifies the current induced in the antenna by the microwaves.

Sensor 640 may also be an RF power sensor to monitor forward and reflected power. The RF power sensor measures the power output of the generator 620 that is utilized by the antenna assembly 610. It can also measure reflected power which is RF energy that is reflected from the ablated tissue region and received by the antenna assembly.

Sensor 640 may also be a pressure sensor for monitoring fluid and/or gas pressure. Pressure sensor generates a signal related to the pressure imposed. Typically, such a signal is electrical, but optical, visual, and auditory signals are not uncommon. Pressure sensors can be classified in terms of pressure ranges they measure, temperature ranges of operation, and most importantly the type of pressure they measure. In terms of pressure type, pressure sensors can be divided into five categories. Absolute pressure sensor which measures the pressure relative to perfect vacuum pressure (0 PSI or no pressure). Gauge pressure sensor is used in different applications because it can be calibrated to measure the pressure relative to a given atmospheric pressure at a given location. Vacuum pressure sensor is used to measure pressure less than the atmospheric pressure at a given location. Differential pressure sensor measures the difference between two or more pressures introduced as inputs to the sensing unit. Differential pressure is also used to measure flow or level in pressurized vessels. Sealed pressure sensor is similar to the gauge pressure sensor except that it is previously calibrated by manufacturers to measure pressure relative to sea level pressure.

Sensor 640 may also be an optical sensor to detect air bubbles or fluid flow. For instance, a light source (not shown) emits a light through the coolant tube in the antenna assembly. The emitted light is reflected by the coolant and is received by an optical sensor. This reflected light is compared to the emitted light and a determination is made as to the presence of an air bubble.

Figure 7:
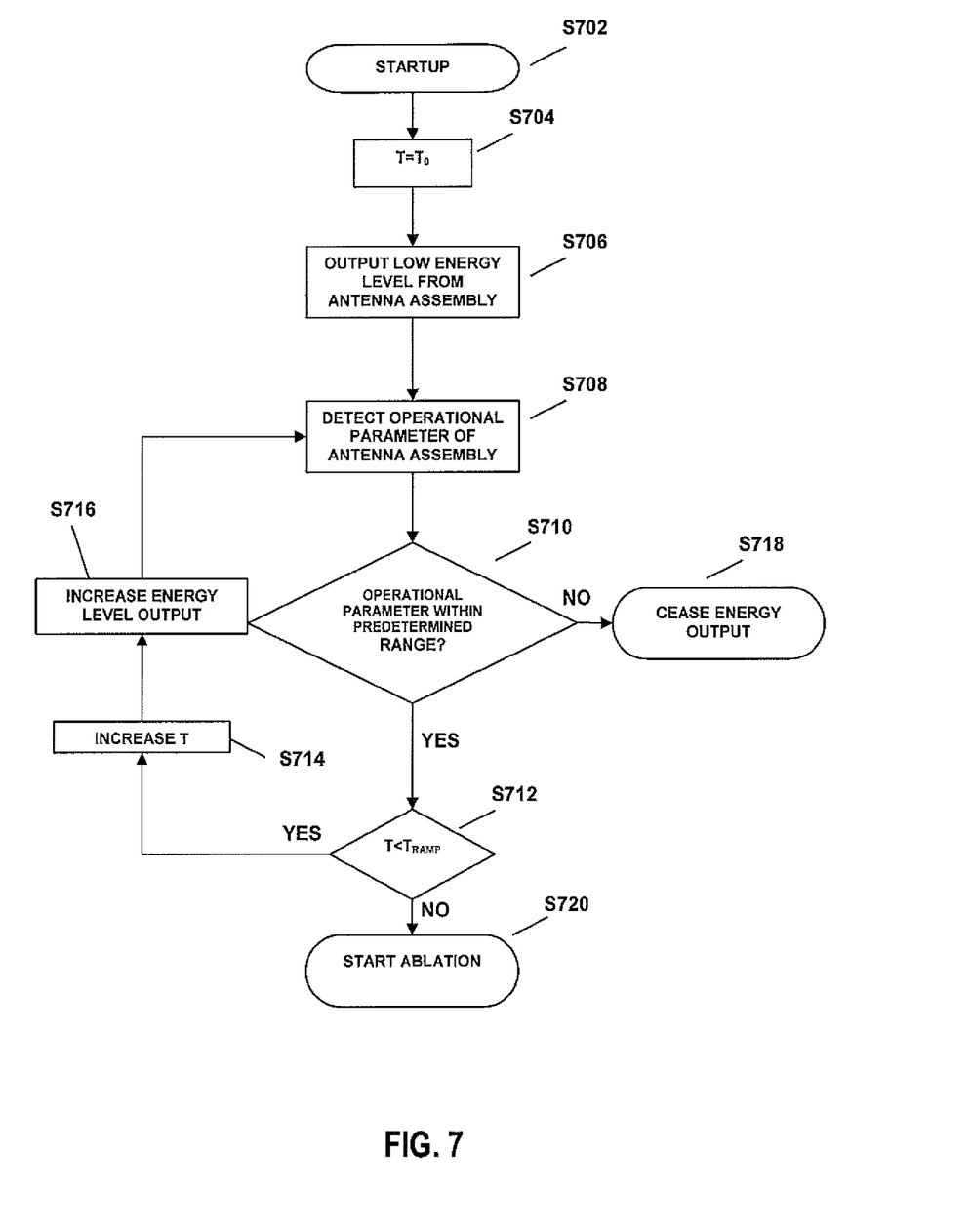
FIG. 7 shows a flow chart describing a ramping procedure according to an embodiment of the present disclosure.

With reference to FIGS. 6 and 7, an operation of the ramping procedure is shown. The procedure starts at S702 where the microwave ablation system 600 is started. At S704, T is set to T0 where T is time and T0 is the initial startup time. At S706, a low energy level is outputted from the generator 620 to the antenna assembly 610. Sensor 640 detects an operational parameter of the ablation probe as described above in S708. In S710, the detected operational parameter is compared to a predetermined range of values stored in controller 630. The predetermined range of values may be set by a clinician or they may be stored in the controller or they may be stored in the microwave or RF probe itself by a manufacturer of the microwave ablation system. If the detected operational parameter is within the predetermined range, the procedure proceeds to S712 where a determination is made as to whether T is less than TRAMP. If T is less than TRAMP, then the procedure proceeds to S714 where T is increased in predetermined intervals. T can be increased in intervals of N seconds or N minutes where N is any positive integer. In S716 the energy level output of the generator 620 is increased and steps S708, S710 and S712 are repeated. When T is no longer less than TRAMP, the procedures proceeds to S720 where the ablation procedure is started and used on a patient. If the controller makes a determination in S710 that the detected operational parameter in S708 is not within the predetermined range, the procedure proceeds to S718 where the controller 630 controls the generator 620 to cease energy output.

The ramping procedure outlined above may avoid an assembly failure and potential clinician or patient injury. Although FIG. 7 depicts a particular arrangement of steps to perform the system check during a ramping procedure, it should be understood that a different arrangement of steps may be used while still falling under the scope of the present disclosure. During the ramping procedure and upon detection of abnormal sensor information, the power ramp would cease and return to zero. The ramp may be made long enough to reliably detect common malfunction mechanisms.

For instance, if the cooling fluid pump is turned off and no fluid is in the antenna assembly, a pressure sensor may return abnormal pressure levels. As such, a power ramp would cease and the power does not reach a level where the coaxial cable would fail due to lack of cooling. If the antenna assembly is full of cooling fluid but the pump is not running, an abnormal reading from the pressure sensor or a rising temperature from a thermo probe would indicate that cooling of the probe is not sufficient most likely due to lack of flow. Therefore, the power ramp would cease and the power does not reach a level where the coaxial cable would fail due to lack of circulation.

In another example, if the device is not inserted into tissue resulting in a dangerous radiation pattern, a radiating detector such as the receiving antenna or rectenna would indicate abnormally high radiating levels along the shaft or around the handle of the antenna. The detection of the high radiating levels would prevent an unintended clinician or patient burn.

When the antenna assembly is subjected to high powers, defects may become readily apparent. On ramp up, the sensors indicate abnormal operating conditions thereby preventing the power level from reaching a level sufficient to cause catastrophic device failure and avoiding clinician or patient injury.

Utilizing a test routine of the ablation probe which gradually subjects the device to increasing operational stresses while monitoring sensor status will allow for MWA systems to limit the number of devices which are damaged due to operator error, such as not turning on the cooling fluid pump. It will also reduce the likely hood of patient and/or user injury from potentially defective assemblies or from user error. This is especially important for high power microwave ablation devices, where failures may result in extremely high temperatures.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A method of detecting an abnormal state in a microwave ablation system, the method comprising the steps of:
outputting a low microwave energy level from a generator to an ablation probe;
monitoring an operational parameter of the ablation probe at the low microwave energy level;
increasing a microwave energy level output of the generator at a constant rate to a predetermined microwave energy level; and
monitoring the operational parameter of the ablation probe while the microwave energy level is increased at a constant rate,
wherein the microwave ablation system ceases output of energy from the generator when the monitored operational parameter is outside a predetermined range.

2. The method according to claim 1, wherein the operational parameter is a temperature of the ablation probe.

3. The method according to claim 1, wherein the operational parameter is a radiating behavior.

4. The method according to claim 1, wherein the operational parameter is forward power or reflected power.

5. The method according to claim 1, wherein the operational parameter is fluid pressure.

6. The method according to claim 1, wherein the operational parameter is the presence of air bubbles.

* * * * *